United States Patent
Zajdowicz

(10) Patent No.: US 9,649,395 B2
(45) Date of Patent: *May 16, 2017

(54) SYSTEMS AND METHODS FOR CLEANING AND DISINFECTING ALLOGRAFT MATERIAL

(71) Applicant: Allosource, Centennial, CO (US)

(72) Inventor: Jan Zajdowicz, Aurora, CO (US)

(73) Assignee: Allosource, Centennial, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 14/857,271

(22) Filed: Sep. 17, 2015

(65) Prior Publication Data

US 2016/0074542 A1 Mar. 17, 2016

Related U.S. Application Data

(63) Continuation-in-part of application No. 13/449,636, filed on Apr. 18, 2012, now Pat. No. 9,138,496.

(51) Int. Cl.
*A61L 2/18* (2006.01)
*A61L 2/00* (2006.01)
(Continued)

(52) U.S. Cl.
CPC .......... *A61L 2/0088* (2013.01); *A61F 2/4644* (2013.01); *A61L 2/0011* (2013.01);
(Continued)

(58) Field of Classification Search
CPC ..... B08B 2209/005; B08B 3/04; B08B 3/044; B08B 3/00; B08B 3/12; B01F 7/02;
(Continued)

(56) References Cited

U.S. PATENT DOCUMENTS 2,406,403 A 8/1946 Rogers
3,819,158 A 6/1974 Sharpe et al.
(Continued)

FOREIGN PATENT DOCUMENTS

WO 00/15328 3/2000
WO 2005/084787 9/2005

OTHER PUBLICATIONS

Microlab, Microgen Bioproducts Newsletter, Pulsifier (Dec. 2004).
(Continued)

*Primary Examiner* — Michael Wieczorek
*Assistant Examiner* — Kevin G Lee
(74) *Attorney, Agent, or Firm* — Sheridan Law, LLC; James A. Sheridan

(57) ABSTRACT

There is disclosed a system for cleaning and disinfecting allograft material. In an embodiment, the system includes a sterile bag and a motorized paddle blender. The sterile bag having an outer wall configured to withstand blending forces, at least one paddle contact section, and an allograft retaining section separate from the at least one paddle contact section. The motorized paddle blender having at least one paddle configured to apply blending forces on the sterile bag on the at least one paddle contact area, a motorized portion to actuate the at least one paddle, and a door component configured to hold the sterile bag adjacent the at least one paddle. The at least one paddle and the allograft retaining section are configured to prevent the paddle from contacting the allograft material when the blending forces are applied on the sterile bag on the at least one paddle contact area.

7 Claims, 11 Drawing Sheets

(51) Int. Cl.
  *A61F 2/46* (2006.01)
  *B08B 3/10* (2006.01)
  *B01F 11/00* (2006.01)
  *A61L 2/025* (2006.01)
  *A61B 50/30* (2016.01)

(52) U.S. Cl.
  CPC ............ *A61L 2/0023* (2013.01); *A61L 2/025* (2013.01); *A61L 2/18* (2013.01); *B01F 11/0065* (2013.01); *B08B 3/104* (2013.01); *A61B 2050/314* (2016.02); *A61B 2050/316* (2016.02); *A61F 2002/4646* (2013.01); *A61L 2202/122* (2013.01); *A61L 2202/17* (2013.01); *A61L 2202/21* (2013.01)

(58) Field of Classification Search
  CPC .......... B01F 7/048; B01F 7/005; B01F 7/085; B01F 7/06; A61L 2/0088; G01N 1/286; G01N 1/34; A61F 2/4644
  USPC ................ 435/1, 267, 268; 604/48; 600/36; 134/169 R, 167 R, 170, 196, 184
  See application file for complete search history.

(56) References Cited

U.S. PATENT DOCUMENTS

| | | | |
|---|---|---|---|
| 4,892,832 A | 1/1990 | Omote et al. | |
| 4,903,718 A | 2/1990 | Sullivan | |
| 5,288,462 A | 2/1994 | Carter et al. | |
| 5,443,801 A | 8/1995 | Langford | |
| 5,556,379 A | 9/1996 | Wolfinbarger | |
| 5,711,921 A | 1/1998 | Langford | |
| 5,846,484 A | 12/1998 | Scarborough et al. | |
| 6,364,520 B1 | 4/2002 | Steele | |
| 6,379,949 B1 | 4/2002 | Ward | |
| 6,416,212 B1 | 7/2002 | Rogers et al. | |
| 6,439,759 B1 | 8/2002 | Ray et al. | |
| 6,613,278 B1 | 9/2003 | Mills et al. | |
| 6,634,783 B2 | 10/2003 | Baron | |
| 7,789,551 B2 | 9/2010 | Ray et al. | |
| 8,117,415 B2 | 2/2012 | Perry | |
| 8,197,117 B2 | 6/2012 | White | |
| 8,272,255 B2 | 9/2012 | Halverson et al. | |
| 2003/0228651 A1 | 12/2003 | Votaw et al. | |
| 2005/0063247 A1 | 3/2005 | Krause | |
| 2005/0078552 A1 | 4/2005 | Zambaux | |
| 2005/0232071 A1* | 10/2005 | Matsumoto | B01F 5/104 366/136 |
| 2007/0009984 A1 | 1/2007 | Votaw et al. | |
| 2007/0140047 A1 | 6/2007 | Ray et al. | |
| 2008/0038364 A1 | 2/2008 | Neely et al. | |
| 2008/0268446 A1 | 10/2008 | Steichen et al. | |
| 2011/0132404 A1* | 6/2011 | Lutz | A61L 2/025 134/19 |

OTHER PUBLICATIONS

Andrews, et al. "Usefulness of the Stomacher in a Microbiological Regulatory Laboratory", Appl. Environ. Microbiol 35(1):89-93, 1978.
Tuttlebee, J.W., "The Stomacher—It's Use for Homogenization in Food Microbiology", Int. J. of Food Sci & Tech. 10(2):113-122, 1975. (Two Page Summary Only).
Johnston, et al., "A Field Study of the Microbiological Quality of Fresh Produce", J. Food Prot. 68(9):1840-1847, 2005.
"Welcome to Seward", Stomacher product information at http://www.seward.co.uk/index.htm, two pages, as accessed on Jul. 16, 2012.
"Sample Preparation Units", Microbiology International Product Descriptions at http://www.800ezmicro.com/products/sample-preparation-units.html, two pages, as accessed on Jul. 16, 2012.
"Stomacher 400 Circulator", Stomacher product brochure, two pages, as accessed on Jul. 16, 2012.
"Stomacher 3500 Series", Stomacher product brochure, two pages, as accessed on Jul. 16, 2012.
"Stomacher Bags", Stomacher product brochure, two pages, as accessed on Jul. 16, 2012.
"Microbiology International", BagMixer product brochure, four pages, as accessed on Jul. 16, 2012.
"Pulsifier", Pulsifier product brochure, one page, as accessed on Jul. 16, 2012.

\* cited by examiner

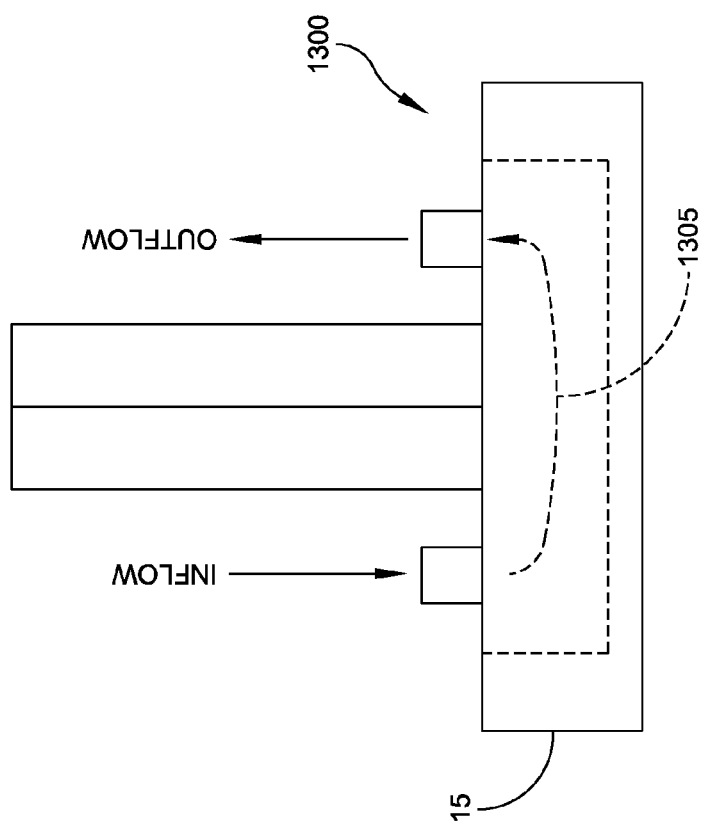

SYSTEMS AND METHODS FOR CLEANING AND DISINFECTING ALLOGRAFT MATERIAL

REFERENCE TO PENDING PRIOR PATENT APPLICATION

This application is a continuation-in-part of prior U.S. patent application Ser. No. 13/449,636, filed Apr. 18, 2012 by Jan Zajdowicz for SYSTEMS AND METHODS FOR CLEANING AND DISINFECTING ALLOGRAFT MATERIAL, which issued on Sep. 22, 2015 as U.S. Pat. No. 9,138,496.

BACKGROUND

The use of musculoskeletal allograft tissue in reconstructive orthopedic procedures and other medical procedures has markedly increased over the last decade. The most common allograft is bone. However, tendons, skin, heart valves and corneas are other common types of tissue allografts.

Prior to use, the allograft tissue must be evaluated for microbial contamination. The allograft product must be tested for bacterial contamination prior to release of the tissue for transplantation. Swabs are widely used in the pharmaceutical and medical device industry for evaluating microbial contaminants on small, hard, non-porous manufacturing equipment, in addition to detecting microbial contaminants in environmental monitoring programs. Some areas of the allograft are simply inaccessible to a swab, thereby not allowing for complete analysis of the allograft for microbial contaminants.

Another method used for detecting microbial contamination on allografts is destructive testing. Destructive testing using companion tissues (small sections of typically lower quality or unusable portions of the allograft) is routinely used to assess microbial contamination on entire allograft lots. This practice has come under intense scrutiny by regulatory agencies since the companion tissue may not be representative of the microbial contamination on entire allograft lot. Furthermore, the geometry of the companion tissue does not adequately represent the geometry of the entire allograft lot.

Recently, non-allograft materials from varying sources (bovine, ceramic, synthetic, etc.) have been used as a representative model of what the allograft tissue products are exposed to during handling and processing. The limitation with these materials is that they are not truly representative of the actual allograft. Furthermore, it is extremely difficult to fabricate synthetic samples to model every product category currently utilized for transplantation.

Prior to use, the allograft tissue must be treated with various agents in order to substantially eliminate microbial contamination as well as clean the tissue of residual blood constituents, bone marrow, residual connective tissue and gross musculature. A variety of cleaning processes have been developed in order to remove contaminants from the allograft and to inactivate microbial contaminants remaining on the allografts. However, these cleaning and inactivation methods are laborious and tedious, and often do not provide a high level of assurance that the allografts have been sufficiently cleaned (e.g., low or inconsistent log reductions in microbial contamination). In particular, many existing allograft cleaning processes require considerable manipulation of the allografts between steps, thus increasing the possibility of environmental cross-contamination. Existing processes also tend to be hard to regulate and control, and their efficacy can be technician dependent. Existing processes also tend to have a shielding or layering effect that can greatly reduce ultrasonic energy penetration and thus not clean as effectively. Furthermore, the shielding effect will also impede the liberation of contaminant microorganisms off of the tissues and into solution where they are more readily eradicated.

Following treatment, allograft products must be tested for bacterial contamination prior to release of the tissue for transplantation. Existing methods of assessing microbial contamination, however, suffer form the same limitations described above (e.g. considerable manipulation between steps, possibility for environmental cross-contamination, hard to regulate and control, technician dependent, etc.).

In the past, ultrasound has been utilized to reduce and/or eliminate microbial contamination of allograft products. Ultrasound is microbiostatic to most microbes, and is used primarily to reduce microbial loads from inanimate objects with specific bactericidal activity on gram-negative bacteria.

With the increased use of allograft products, there is a need to provide improved methods and apparatus for treating allografts in order to help provide the cleanest and safest allografts as well as confirm that the allografts are free from bacterial contamination.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

In an embodiment, there is provided a system for cleaning and disinfecting allograft material, the system comprising a sterile bag having an outer wall configured to withstand blending forces, at least one paddle contact section, and an allograft retaining section separate from the at least one paddle contact section; a motorized paddle blender having at least one paddle configured to apply blending forces on the sterile bag on the at least one paddle contact area, a motorized portion to actuate the at least one paddle, and a door component configured to hold the sterile bag adjacent the at least one paddle, wherein the at least one paddle and the allograft retaining section are configured to prevent the paddle from contacting the allograft material when the blending forces are applied on the sterile bag on the at least one paddle contact area.

In another embodiment, there is provided a process of cleaning allograft material, the process comprising staged, continuous, or both staged and continuous solution fluid pumping into the bag system.

In yet another embodiment, there is provided a process of disinfecting allograft material with an allograft microbial extraction process.

In still another embodiment, there is provided a process of demineralizing allograft material with an acid solution.

In another embodiment, there is provided a process of preparing allograft material with an allograft viability promotion process.

In still yet another embodiment, there is provided a process of preparing allograft material with a final packaging process.

Other embodiments are also disclosed.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which:

FIG. 13 illustrates a hollowed port system within a paddle configured to provide temperature control.

DETAILED DESCRIPTION

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

A blender and bag combination device and process is provided such that allograft material can be effectively cleaned (e.g., removal of blood, lipid, and proteins) and disinfected (e.g., removal and killing of bacteria and fungi). This technology can also be utilized to promote microbial removal of microorganisms for sampling and detection purposes.

Secondary uses of the blender and bag combination include, but are not limited to, demineralization of bone and promotion of chondrocyte viability in joint restoration allografts.

In an embodiment, a blender device may be used to liberate microbes from allograft material. The blender device may be a Stomacher brand device with modified paddles to prevent homogenization of the allograft material. Traditional Stomacher brand blenders apply paddles to a sterile bag (e.g., the internal surfaces of the bag are sterile) with contents until the contents are blended into a homogenized state. This is an example of a destructive test that differs significantly from the blender device and methods for non-destructively testing, cleaning and disinfecting allograft material. In either a destructive test or a non-destructive test (as described hereinbelow), Microorganisms are generally liberated from the tissue do to the back-and-forth direction of the liquid within the bag (i.e., the turbulent nature of the liquid.)

In one exemplary embodiment, a rectangular bag receives and retains allograft material within the central portion of the bag using screen material, which may be heat-sealed internally to the bag. The entry point of the allograft into the bag may also be heat sealed to create a closed system. The bag can be filled with solution liquid (e.g., cleaning solution, microbial extraction solution, or other suitable allograft wash solution) using bag ports. This bag system can be placed into an additional mechanical blending system.

A motorized driven device provides paddles contact the left and right portions of a rectangular-shaped bag. The paddles alternate back and forth at high speed to force the liquid within the bag to move left-to-right and right-to-left through and over the allograft material retained in the center of the bag. This liquid turbulence removes contamination and provides excellent mechanical cleaning of the allograft material. The spent liquid can be ported off, physically removing soil and contamination, and new solutions can be ported into the bag as needed.

Figure 2:
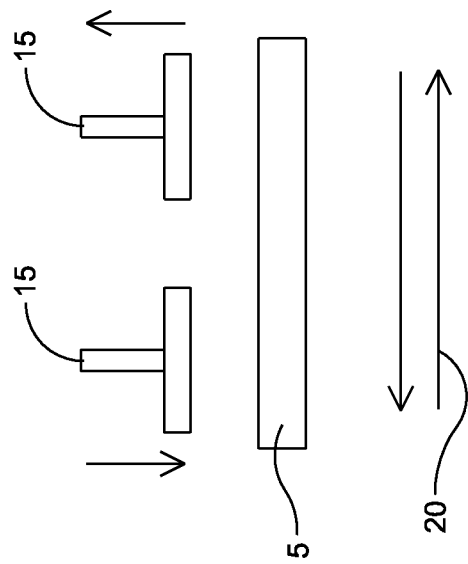
FIG. 2 illustrates a top view of a prior art sterile blender bag of FIG. 1 with liquid solution for blending with paddles to cause liquid solution to reciprocate in the general directions as shown with arrows.
Figure 1:
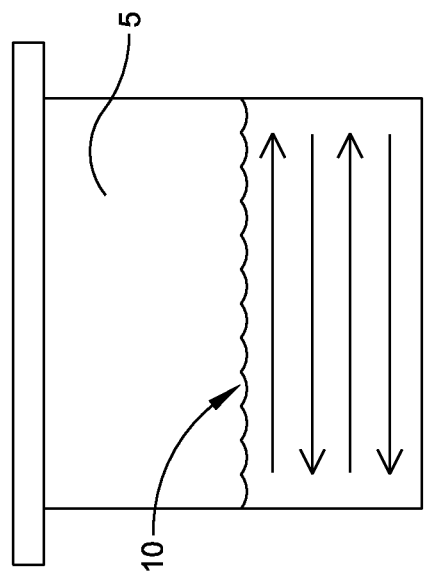
FIG. 1 illustrates a side view of a prior art sterile blender bag with liquid solution for blending with paddles to cause liquid solution to reciprocate in the general directions as shown with arrows.

With reference to FIGS. 1 and 2, and as disclosed in the prior art, a sterile bag 5 may be provided with liquid solution 10 for blending with paddles 15 to cause liquid solution 10 to reciprocate in the general directions as shown with arrows 20. FIG. 1 illustrates a side view of bag 5 and FIG. 2 illustrates a top view of bag 5.

Figure 3:
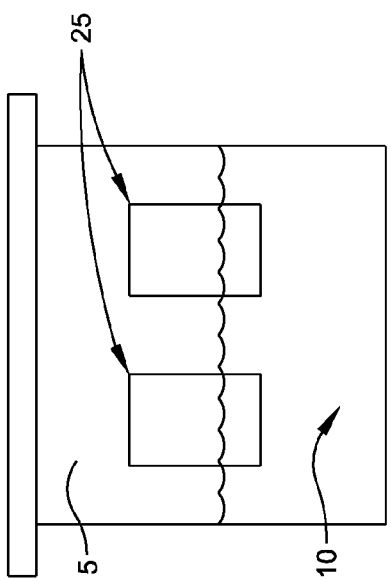
FIG. 3 illustrates a prior art sterile bag having regions for paddle contact which are very close to one another to agitate fluid and any other contents.

With reference to FIG. 3, and as disclosed in the prior art, sterile bag 5 may include regions for paddle contact 25 which are very close to one another to agitate fluid 10 and any other contents. This traditional bag design, with a traditional paddle design of a blender, causes the homogeneous blending as referred to hereinabove. With the paddles positioned next to one another, any soft tissue within the bag 5 will eventually be pummeled. This is true for soft tissue or any tissue. This is an undesirable configuration inasmuch as the allograft material will ultimately be rendered unusable.

Figure 4:
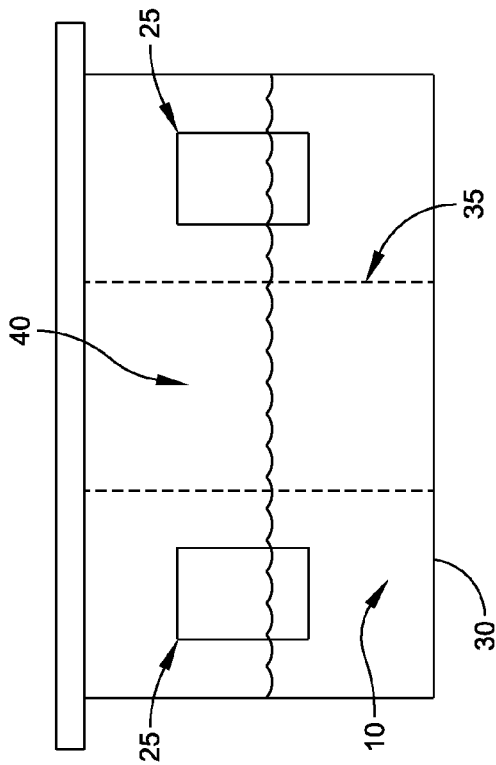
FIG. 4 illustrates an allograft blender bag provided with an internal screen for retention of allograft material in a location.

With reference now to FIG. 4, and in an embodiment, an allograft bag 30 may be provided with an internal screen 35 for retention of allograft material in a location 40. This positions the tissues in a central portion of the bag and allows paddles to be separated to flanking portions beyond the position of this central portion to cause turbulent fluid flow while simultaneously avoiding tissue pummeling. This motion of the solution liquid will liberate microorganisms from the graft in the central portion.

In an embodiment, the screen material 35 is heated-sealed into the center portion (location 40) allowing for the retention of allograft material. This screen is designed to hold the allograft material, not allowing it to drift in the bag 30, so as to prevent paddle contact, which may crush and destroy the valuable allograft material. Likewise, the screen material 35 will allow the liquid to make contact (through the open pores) with the allograft material when it is forced back and forth via paddle contact with the bag. Multiple ports are integrated into the bag whereby fluid can be added and removed from the bag as needed.

Allograft bag 30 together with an appropriate blending machine may be used for bioburden assessment. This assessment may occur immediately prior to disinfection procedures to assess bioburden of the allograft material. This assessment may occur immediately after disinfection procedures to assess bioburden of the allograft material.

Figure 12:
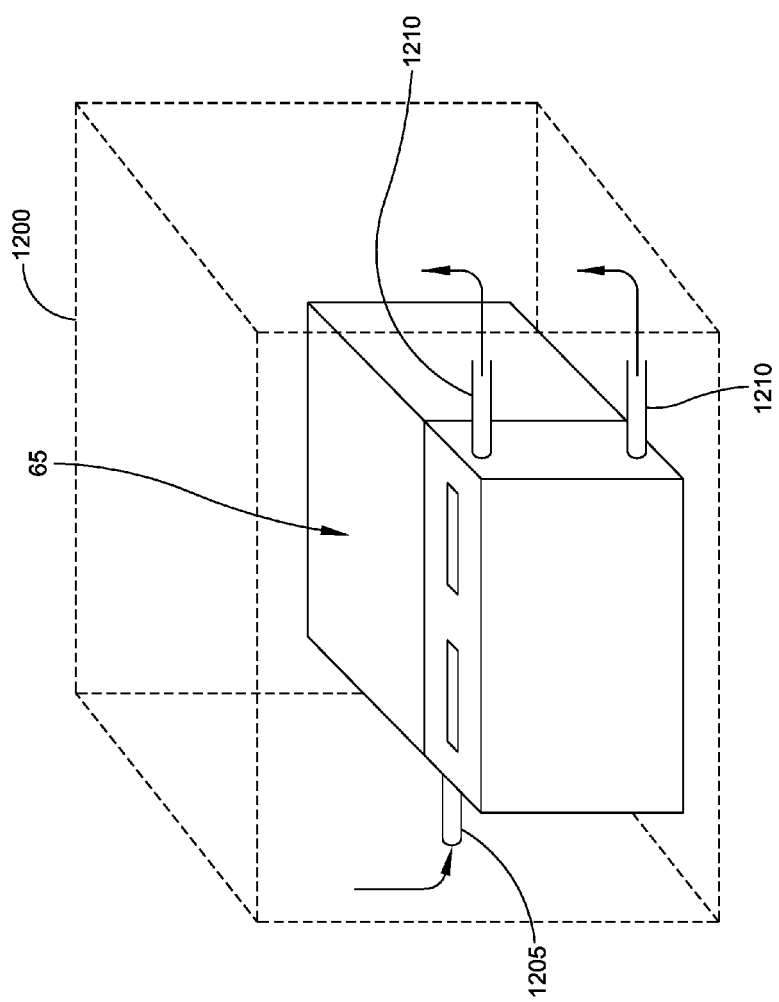
FIG. 12 illustrates an ultrasonic water bath configured to control temperature of an allograft material.

With reference to FIG. 12, ultrasonic technologies may be combined with the blender 65 depending on the type of graft. The entire system, e.g., bag system and paddle system, may be submerged within an ultrasonic water bath 1200. The mechanical washing from the paddles may become more efficient when in conjunction with ultrasonic cleaning. The temperature of the allograft material within the bag may be controlled though the ultrasonic water bath. An exterior inlet port 1205 and an exterior outlet port 1210 may be fluidly coupled with an exterior of the motorized paddle blender. Exterior inlet port 1205 and exterior outlet port 1210 may be located such that the agitated fluid flows through the exterior inlet port from the ultrasonic water bath into the motorized paddle blender, across the outer wall of the sterile bag, and through the exterior outlet port back into the ultrasonic water bath.

In an embodiment, and with reference to FIG. 13, a hollowed port system 1300 may be provided within the paddles 15. This port system within the paddle may provide temperature-controlled solution 1305 constantly pumped through each of the paddles 15 to maintain a desired temperature or temperature range during a processing embodiment. Long processing times with the paddling unit will most likely generate heat, thus, by porting temperature-controlled solution through the paddles 15 the cooled device may ensure constant temperature exposure (e.g., no increase of heat) to the allograft material.

In another embodiment, a higher temperature (e.g., 45 degrees C.) may be desired to promote higher level of cleaning and disinfection. In another embodiment, a lower temperature (e.g., 4 degrees C.) may be required to promote cellular viability. The hollowed port system may provide temperature regulation for either, or both, of a higher temperature or a lower temperature.

Figure 5:
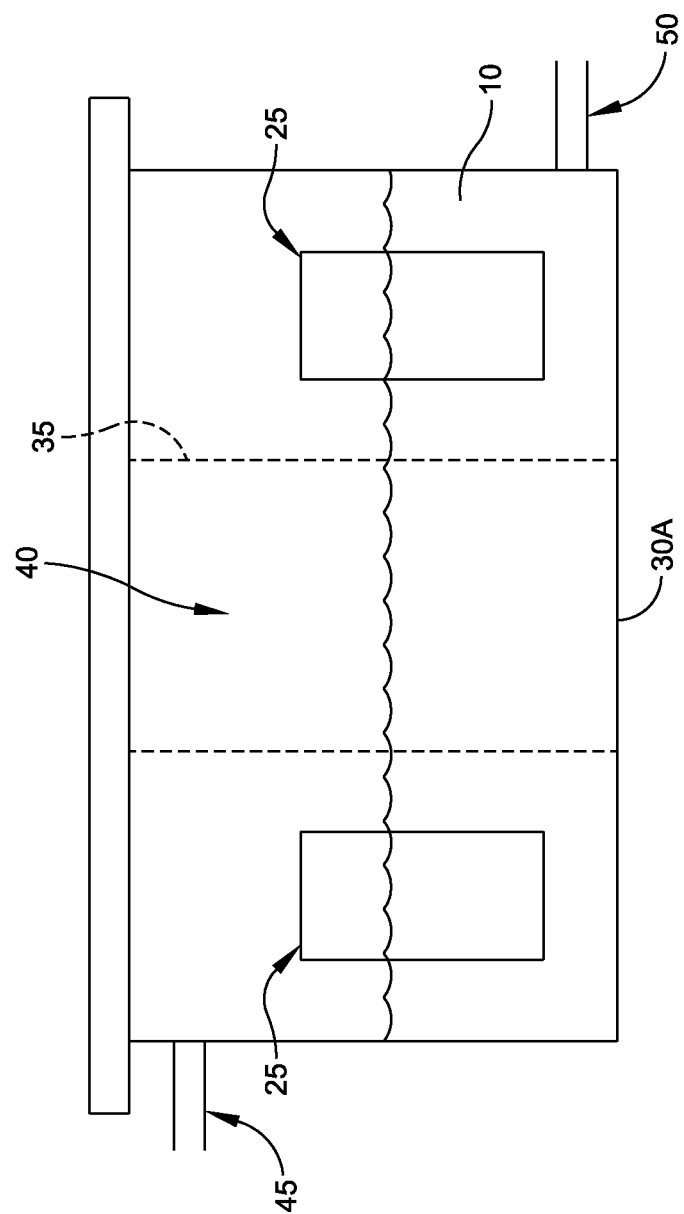
FIG. 5 illustrates an allograft blender bag may be provided with an inlet port and an outlet port to handle the flow of fluid.

In another embodiment, and with reference to FIG. 5, an allograft bag 30A may be provided with an inlet port 45 and an outlet port 50 to handle the flow of fluid 10. During operation with forces applied by one or more paddles to one or more contact areas 25, fluid 10 may be circulated through bag 30A with a graft sealed in location 40.

Bag 30A may be loaded at the beginning of a disinfection procedure and solution liquid may be pumped in while forces are applied by one or more paddles to one or more contact areas 25. During each step within a disinfection procedure, bag 30A could be paddled to force the disinfection solution in and around the graft. Because the graft is retained within the bag, disinfection procedures may require very minimal handling of the graft.

Solution liquids of one or more types may be flushed through bag 30 (e.g., not paddled) to minimize or eliminate any bacteriostatic problems that residual disinfection chemicals may cause for taking post-bioburden samples.

Figure 6:
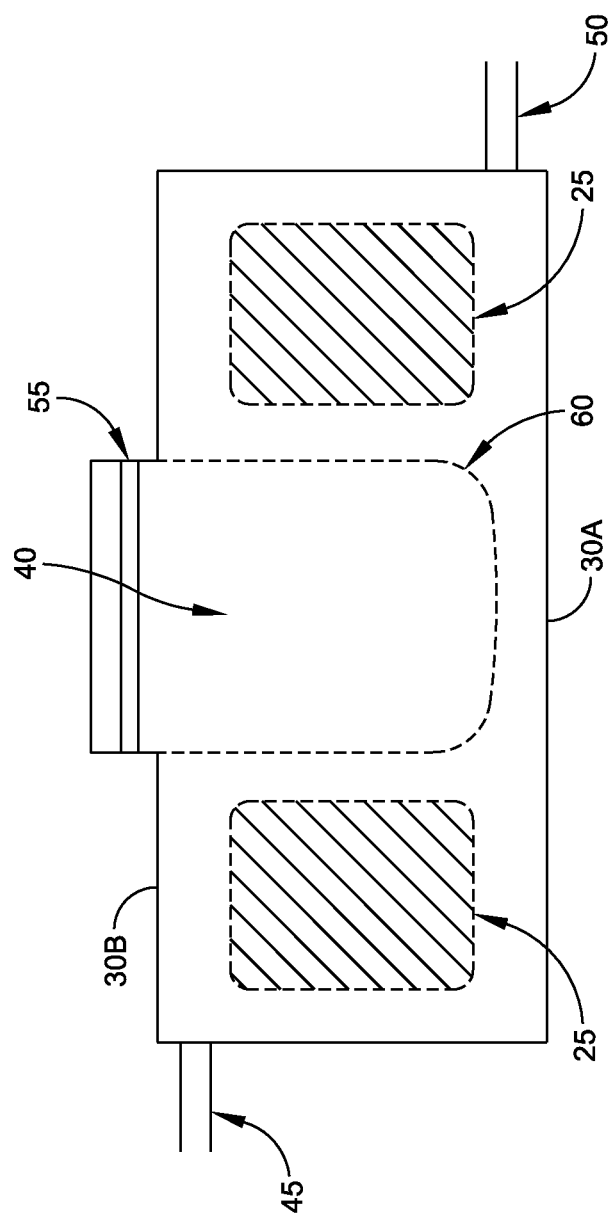
FIG. 6 illustrates a heat-sealable tab and screen material provided in a blender bag system.

In one embodiment, and looking at FIG. 6, a heat-sealable tab 55 and screen material 60 may be provided in a bag 30B. Heat-sealable tab 55 and screen material 60 may form the location 40 for retention of allograft material. After placement of the allograft material within bag 30B, tab 55 may be heat sealed to hold graft material. As discussed above with respect to bag 30A, inlet port 45 and outlet port 50 may be provided in bag 30B to handle the flow of fluid 10.

Figure 7:
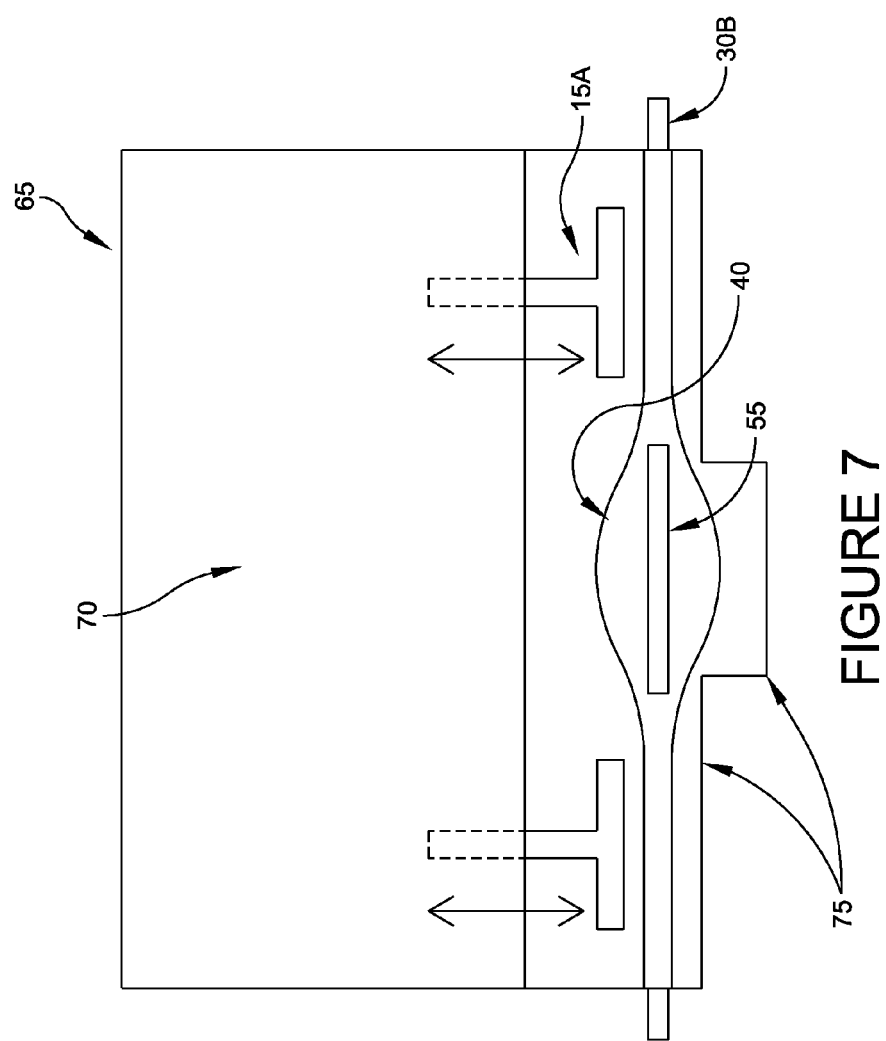
FIGS. 7 and 8 illustrate a blender machine for selectively applying paddling forces to any one of the blender bags.
Figure 8:
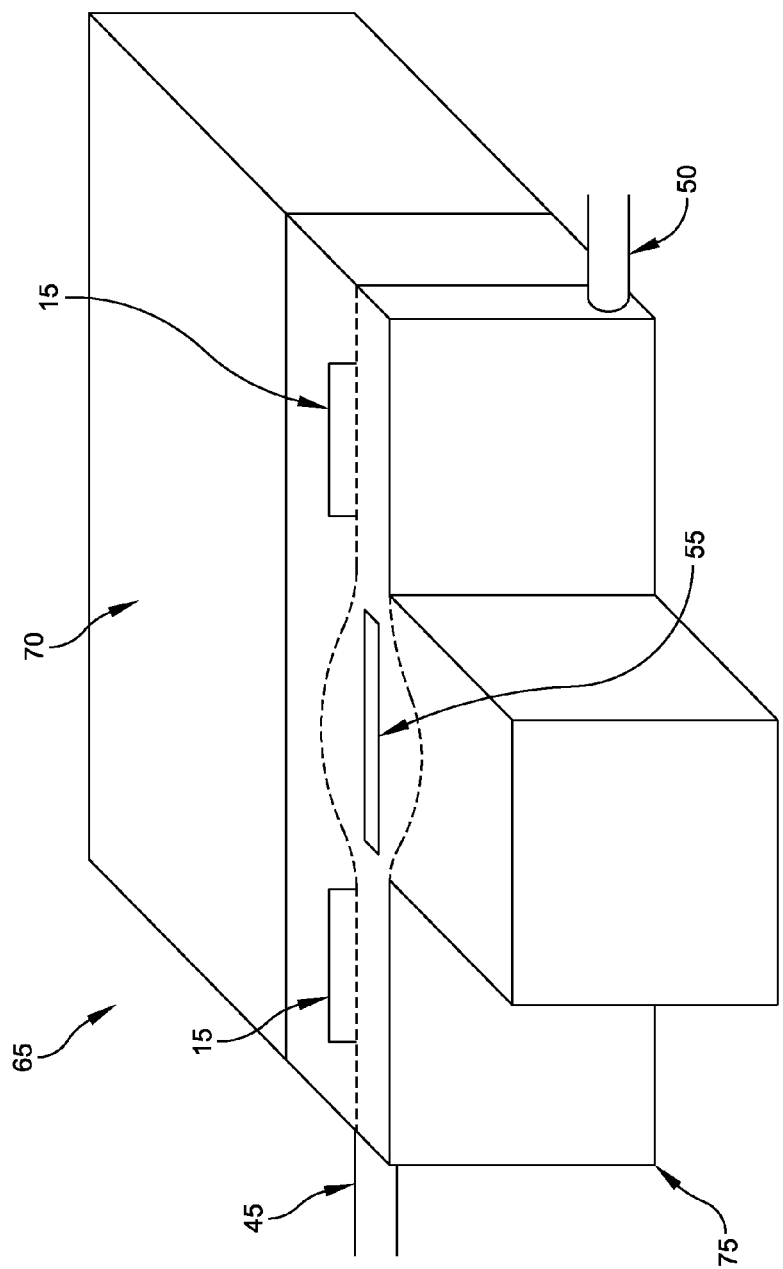

With reference now to FIGS. 7 and 8, and in an embodiment, a blender machine 65 may be provided for selectively applying paddling forces to any one of bags 30, 30A, 30B, or 30C (discussed below.) A motorized portion of blender machine 65 may be configured to appropriately actuate separated paddles 15A for application of forces to the inserted bag 30, 30A, 30B, or 30C. A door component 75, or other retention mechanism, may be configured to position and maintain bag 30, 30A, 30B, or 30C with respect to paddles 15A. As shown in FIG. 7, paddles 15A are positioned apart from one another to provide a graft retention location 40, which allows fluid flow with adequate force and prevents the homogeneous blending of the allograft material. Bag 30, 30A, 30B, or 30C may be filled to a predetermined volume but should not be overfilled to prevent bursting under paddle pressure.

In another processing embodiment, an allograft viability promotion process may include processing "fresh grafts" with live cells MEM (culture media)/antibiotic combinations. Fresh cartilage grafts contain chondrocytes that must remain viable for successful transplantation. An alternative use of bag system with the blender system may implement minimal essential media (MEM) incubation of these fresh cartilage grafts.

Fresh sterile MEM may be ported into the bag system to bathe the graft and promote cellular viability. The paddle system may be programmed such that instead of alternative paddling at high speeds to promote cleaning, a single paddle could be set to apply selective, steady force to create hydrostatic pressure (e.g., 10-100 psi) within the bag. At selective times during the fresh cartilage graft incubation period, these pressures could be applied in short intervals. This pressure would imitate water pressures within in vivo joints, which could promote cellular viability within the cartilage. Media changes may involve brief alternative paddling followed by fresh MEM ported into the bag after old MEM is removed from the bag.

In one embodiment, and due to the separation of the paddles, reciprocation of the paddles may not be necessary and the paddles may push in tandem forcing liquid from the lateral portions of bag 30, 30A, 30B, or 30C to the central portion 40. In another embodiment, one of the paddles may be configured to extend a greater distance into bag 30, 30A, 30B, or 30C than the other paddle. Leaving open inlet port 45 and outlet port 50, and providing an in-line stream of solution liquid 10 through the bag 30, 30A, 30B, or 30C. This can provide a cleaning effect and a recirculating effect (i.e., bringing in fresh solution.)

Depending on the graft material, more than one specimen could be added to bag 30, 30A, 30B, or 30C. Additional separations could be included to either keep fluid within an area of a particular graft or to allow fluid flow to multiple grafts (i.e., graft materials from a single donor.)

Figure 9:
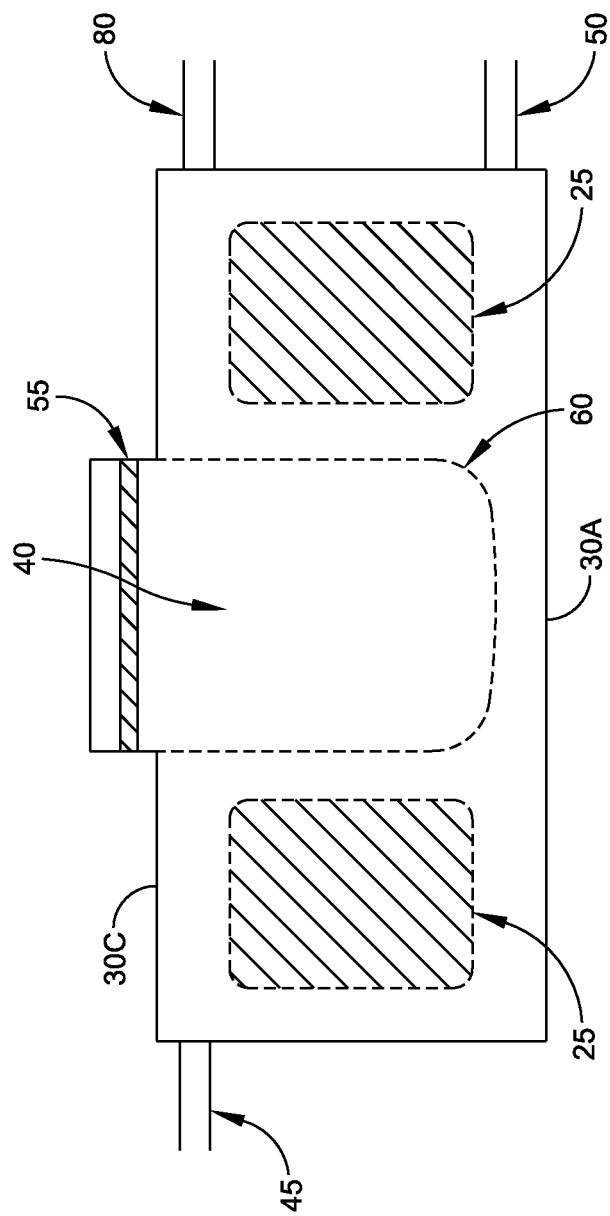
FIG. 9 illustrates an air purge extending through the sidewall of a blender bag.

In another embodiment, and referring now to FIG. 9, an air purge 80 may extend through the sidewall of a blender bag 30C. For initial filling of disinfection solution, air purge 80 is necessary to allow air to escape. Air purge 80 may include a filter to prevent contamination to the graft materials or solution fluid 10. Similar to the other blender bags described hereinabove, side portions for paddle contact areas 25 may be provided by blender bag 30C. A central area 40 may be configured for retaining a graft away from paddle contact areas 25. Heat-sealable tab 55 and screen material 60 may form the location 40 for retention of allograft material in blender bag 30C. Inlet port 45 and outlet port 50 may be included on bag 30C.

Figure 10:
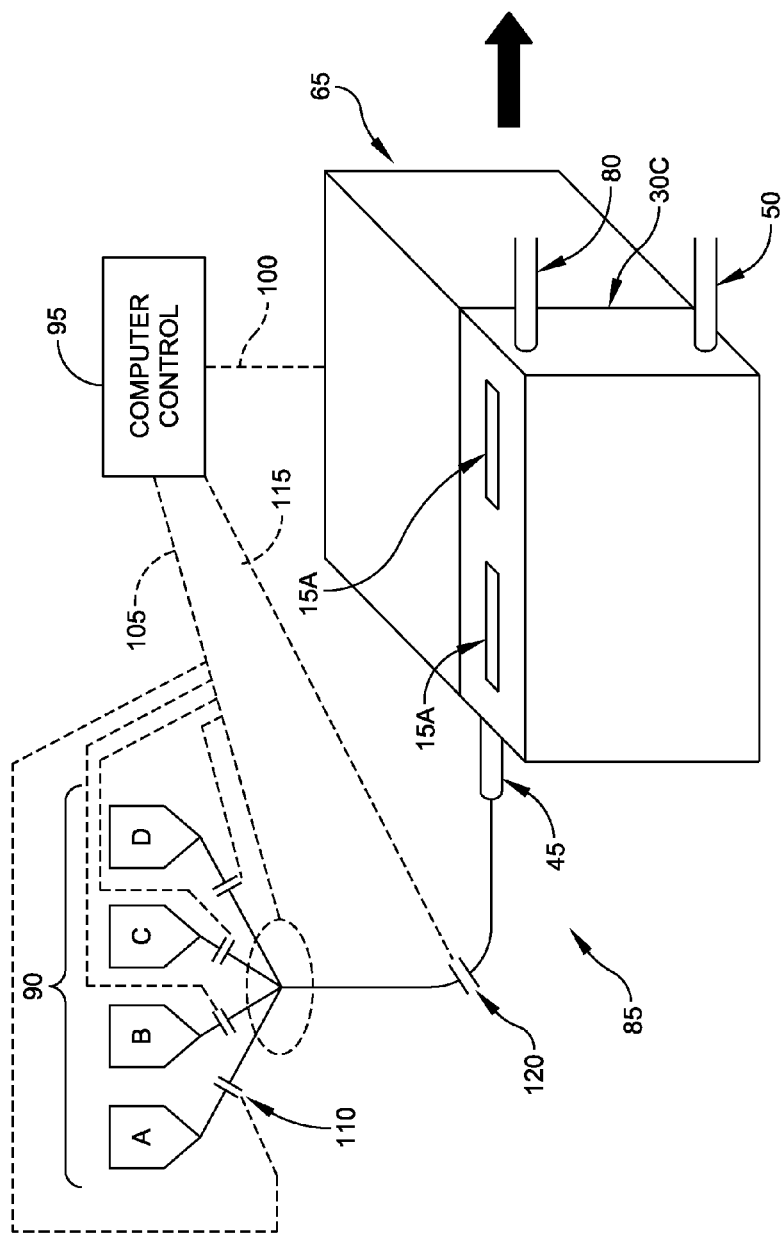
FIGS. 10 and 11 illustrate an array of tissue treatment solutions operatively connected to an inlet port of the blender bag and a computer controller for fluid delivery.
Figure 11:
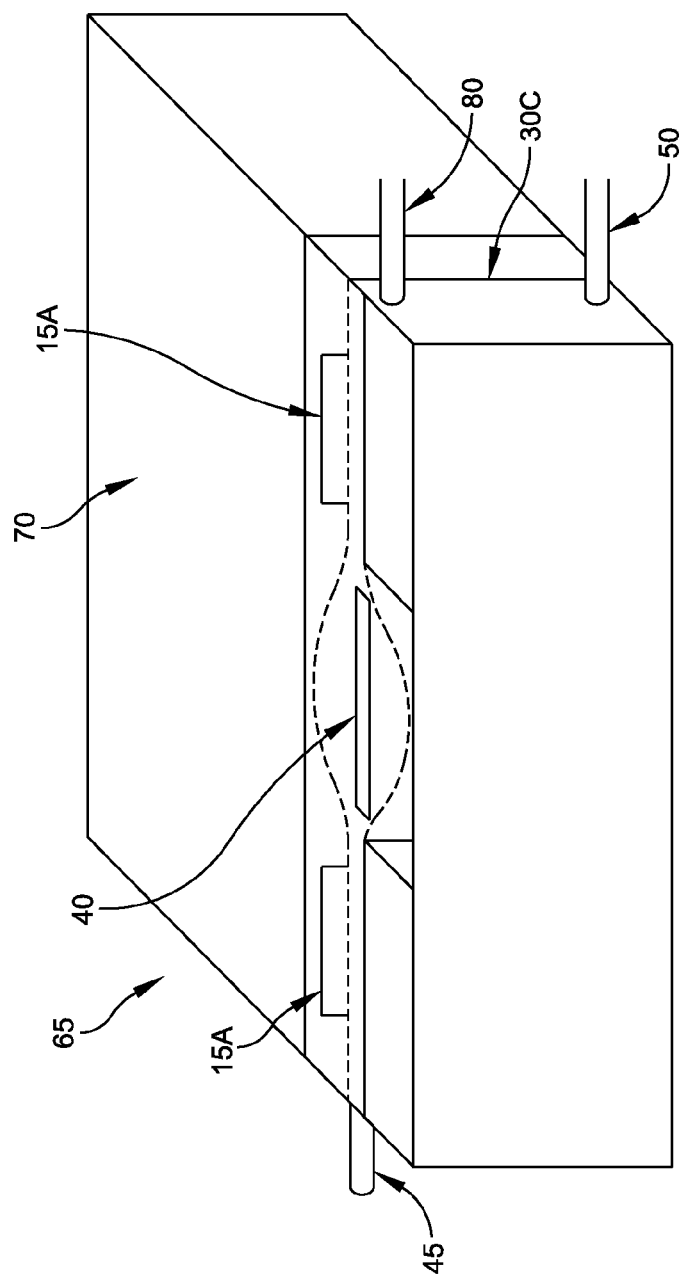

With reference to FIGS. 10 and 11, an array 90 of tissue treatment solutions may be operatively connected to inlet port 45 of bag 30C (or another appropriate bag) and fluid delivery may be selectively operable by computer controller 95. Paddling blender machine 65 and associated valves may be computer controlled to maintain set process parameters. Communication conduit 100 and communication conduit 105 may be provided from computer controller 95 to blender machine 65 and tissue treatment solutions array 90, respectively. These conduits may include wired or wireless communications. A valve system 110 may be operated by computer controller 95 to regulate fluid dispensing by array 90 and may be operatively connected with communication conduit 100 to computer controller 95. A communication conduit 115 may control an additional valve 120 between array 90 and inlet port 45. This conduit may include wired or wireless communication.

One paddle 15A may be offset with respect to the other paddle 15A so as to compress solution liquid 10 slightly more than the other paddle. This causes blending and creases a pressure gradient to force solution to a waste location from outlet port 50. With the valve of outlet port 50 open, and the blender 65 on, solution liquid 10 is blended across allograft tissue material and solution liquid 10 is slowly taken away to a waste location from outlet port 50.

With the valve of outlet port 50 closed, and the blender 65 on, solution liquid 10 is blended across allograft tissue material and solution liquid 10 is retained within bag 30c instead of taken away to a waste location from outlet port 50.

With the valve of outlet port 50 open, and the blender 65 off, solution liquid 10 is solution liquid 10 is run across (i.e., flushes) across allograft tissue material and taken away to a waste location from outlet port 50 at the speed of the pull of gravity.

In an exemplary embodiment, an allograft cleaning process may include the follow procedure. Upon sealing allograft material into the screened portion of the bag, various detergent, disinfectant, chemical sterilant, and microbial extraction solutions may be pumped into the bag. This solution pumping is either stages, continuous, or a combination of both stages and continuous solution pumping.

A stage scenario may include pumping a certain solution into the bag, executing a timed paddling process, and finally evacuating the bag. This process may be continued with additional solutions.

A continuous scenario may include pumping solutions into the bag while the paddling process is continuous. The evacuation port would essentially be left open as one or more new solutions are being pumped into the bag system.

If one paddle is allowed to compress further than the other paddle, it is theorized that this could create an imbalance whereby fresh solution could be drawn into the bag thus creating a scenario in "continuous" mode where solution is likewise forced out the outlet port. This could mean no external pumps would be needed for this scenario.

A combination scenario may include steps that follow a staged flow and others with a continuous flow.

An allograft microbial extraction process may include a defined speed and time of the paddles using a microbial extraction solution or sterile water. High extraction efficiency may be achieved using a paddling methodology. The solution taken from the outlet port may be used for microbial detection analysis (e.g., real time PCR, fluorescent laser scanning, traditional microbiological analysis, etc.)

In another processing embodiment, an allograft demineralization process may be provided in addition to cleaning allograft material. Depending on the solution fluid, e.g., an acid solution, the mechanical washing effect of the bag paddling could also provide efficient bone demineralization. The paddle agitation surrounding the mineralized allograft material may be advantageous as fresh solution is ported into the bag and allowing for "spent" acid solution to be ported away.

Additionally, all spent solutions ported off from the bag system in may be taken for microbiological analysis to verify in process control of the allograft cleaning process.

In another embodiment, an allograft final packaging process may be provided using the bag system. One of the advantages of the bag system is containing the tissue in a closed environment. Following a post-processing final tissue assessment, which may involve technician handling and any final debridement, the tissue may be placed into a new sterile bag system and then undergo some final disinfection and rinsing steps. The bag system could be then be minimally modified (e.g., ports sealed, etc.) to become the final packaging for the allograft material.

Paddling blender 65 and any of bags 30, 30A, 30B, or 30C may be sized large enough to disinfect all currently processed graft sizes.

Paddling Parameters

To obtain adequate fluid motion within the bag to initiate microorganism release from the tissue graft or the tissue grafts, in an embodiment, the paddling may be between 300-800 paddle compressions a minute for both of the paddles. Using a stomacher machine, 1 rotation provides 2 compressions (i.e., one compression for each paddle per rotation.) This configuration may provide 150 to 600 paddle compressions for a stomacher machine with an operating range of 75-300 RPM. Other operating ranges may provide other amounts of paddle compressions. The shear forces generated within this range will be sufficient to remove microorganism contamination from the tissue grafts(s).

Ultrasonic Parameters

If this device is used within an ultrasonic water bath, the unit must be outputting at a frequency of 40-150 kHz at a power setting of 50-300 Watts per gallon.

Flow Parameters

This setting can be highly variable depending on the desire addition and removal of solution from the bag. Optimally, a setting of 1 mL per second will suffice.

Temperature Parameters

The solution within the bag system may be operated between 4-55 degrees C. depending on the desired temperature setting. Higher temperatures are desired for microorganism kill and lower temperature are desired for allograft cell viability (e.g., chondrocyte, fibroblasts).

Example 1

The following processing example relates to processing a fresh cartilage graft. This is a processing example, thus, types of solutions, steps, and processing times may be changed or modified.

Tissue may undergo typical debridement and processing steps whereby surrounding unwanted tissue are removed from the cartilage. Any other processing could occur at this stage (e.g., centrifugation).

Debrided grafts may be placed into the bag system and the bag may be sealed.

MEM solution may be ported into the bag using a staged processing scenario. The paddles may be maintained at a temperature of 22 degrees C. using flowing solution. For 5 minutes, the paddles are moved at high speed. An exemplary range of high-speed paddle movement is 300 RPM. The solution may be ported off (and may be sampled for microbial contamination.)

MEM solution containing an antibiotic cocktail may be ported into the bag system. The flow juncture to the paddles may be switched to maintain a temperature of 32 degrees C. For 5 minutes, the paddle will be allowed to move at high speed. The solution may sit unanimated for the following 15 minutes. This may be repeated (5 minute paddling+15 incubation) two more times to make a total MEM antibiotic exposure 1 hour. The solution may be ported off (and may be sampled for microbial contamination).

MEM solution containing an antibiotic cocktail may be ported into the bag system. The flow juncture to the paddles may be switched to maintain a temperature of 32 degrees C. For 5 minutes, the paddles will be allowed to move at high speed. The solution may sit unanimated for 15 minutes. This may be repeated (5 minute paddling+15 incubation) two more times to make a total MEM antibiotic exposure 1 hour. The solution may be ported off (and may be sampled for microbial contamination).

MEM solution (no antibiotics) may be ported into the bag system. The flow juncture of the paddles may be switched to maintain a temperature of 22 degrees C. No paddling occurs for a 5-minute exposure. The solution may be ported off (and may be sampled for microbial contamination).

The bag would be opened to allow for the technician to perform any final debridement and/or "other/outside" of the bag system processing steps with the tissue. The bag will be discarded.

The graft may be placed into a fresh sterile bag system. MEM solution (no antibiotics) may be ported into the bag system. A two-minute exposure to the high-speed paddles may be followed by the MEM solution ported off into a sterile vessel for microbial contamination assessment. This may be designated as the final/pre-incubation culture.

MEM solution containing Bacitracin (50 U/mL) and Polymyxin B (500 U/mL) may be ported into bag system. The flow juncture to the paddles may be switched to maintain a temperature of 4 degrees C. AlloPulse may be set to perform incubation processing described in Process Embodiment D. Once an hour, the bag may be gently compressed to achieve a positive hydrostatic pressure within the bag system solution of 25 psi (this hold will last two minutes). The solution may be held in the bag for no more than 48 hours.

On or before 48 hours (4 degrees C.), the MEM will be ported off (solution can be assayed for contamination-real time analysis) from the bag system and fresh MEM containing Bacitracin/Polymyxin B may be ported into the bag. Once an hour, the bag may be gently compressed to achieve a positive hydrostatic pressure within the bag system of 25 psi (this hold will last two minutes). The solution will be held in the bag for no more than 48 hours.

A final real-time microbial assessment can be made immediately prior to graft release.

With the bag system contain the graft and MEM with Bacitracin/Polymyxin B, the bag system may be sealed off and become the final packaging used to distribute the graft.

Example 2

The following processing example is a reflection of above-mentioned embodiments with regard to processing a traditional allograft (e.g., tendon or tricortical wedge). This is merely a processing example, thus types of solutions, steps, and processing times may change.

Tissue may undergo typical debridement and processing steps whereby surrounding unwanted tissues are removed from the tissue. Shaping and cutting of allograft may be performed. Any other pre-bag system processing could occur at this stage (e.g., centrifugation). It is recommended that a centrifugation step precede the bag system steps.

Debrided and shaped grafts would be placed into the bag system and the bag may be sealed.

Bacitracin (50 U/mL)/Polymyxin B (500 U/mL) cocktail solution may be ported into the bag using a staged processing scenario. The paddles may be maintained at a temperature of 37 degrees C. using flowing solution. For 5 minutes, the paddles are moved at high speed. In an exemplary embodiment, the range of high-speed paddle movement may be 300 RPM. The solution may sit unanimated for 15 minutes. This may be repeated (5 minute paddling+15 minute incubation) two more times to make total Bacitracin/Polymyxin B cocktail exposure 1 hour. The solution may be ported off (and may be sampled for microbial contamination.) This step may be repeated if necessary.

3% Hydrogen Peroxide solution may be ported into the bag using a staged processing scenario. The paddles may be maintained at a temperature of 45 degrees C. using flowing solution. For 5 minutes, the paddles operated at high speed. The solution may sit unanimated for 15 minutes. This may be repeated (5 minute paddling+15 incubation) two more times to make total 3% $H_2O_2$ cocktail exposure for 1 hour. In an embodiment, a one-way check valve may be provided through the bag for outgassing. An additional tube may be attached to inlet port 45 and may be positioned above the bag to allow only gas to vent from the bag. The solution may be ported off (and could be sampled for microbial contamination.) This step may be repeated if necessary.

The bag may be opened to allow for the technician to perform any final debridement and/or "other/outside" processing steps with the tissue. The bag may be discarded.

The graft may be place into a fresh sterile bag system. Sterile water may be ported into the bag system. For 5 minutes, the paddles are operated at high speed. The solution may sit unanimated for 15 minutes followed by 5-minute high-speed paddle step. The solution may be ported off (and could be sampled for microbial contamination). This step may be repeated if necessary.

Sterile water may be ported into the bag system. A two-minute exposure to the high-speed paddles may be followed by the water ported off into a sterile vessel for microbial contamination assessment. This may be designated as the final culture.

The bag system containing the graft may be sealed off, frozen down, and become the final packaging used to distribute the graft.

Example 3

The following processing example is a reflection of above-mentioned embodiments with regard to demineralizing bone. This is merely a processing example, thus, types of solutions, steps, and processing times may change.

Milled tissues to particular specifications (e.g., particle range) may be added into the bag system and the bag may be sealed. The pore size within the screened material within the center of the bag may need to be of sufficient size not to let said particle range escape from the center portion of the bag.

0.5 N Hydrochloric Acid would be ported into the bag using a staged processing scenario. The paddles would be maintained at a temperature of 22 degrees C. using flowing solution. For 5 minutes, the paddles may operated at high speed. The solution may sit unanimated for 15 minutes followed by a 5-minute high-speed paddle step. The solution may be ported off (and may be sampled for residual calcium), This step may be repeated as necessary.

Sterile Water may be ported into the bag using a staged processing scenario. The paddles may be maintained at a temperature of 22 degrees C. using flowing solution. For 5 minutes, the paddles will be operated at high speed. The solution may sit unanimated for 15 minutes followed by a 5-minute high-speed paddle step. The solution may be ported off (and may be sampled for residual calcium.) This step may be repeated as necessary.

Sodium Phosphate Buffer Solution may be ported into the bag using a staged processing scenario. The paddles may be maintained at a temperature of 22 degrees C. using flowing solution. For 5 minutes, the paddles may be operated at high speed. The solution may sit unanimated for 15 minutes followed by a 5-minute high-speed paddle step. The solution may be ported off (and may be sampled for residual calcium). This step could be repeated as necessary.

Sterile Water may be ported into the bag using a staged processing scenario. The paddles may be maintained at a temperature of 22 degrees C. using flowing solution. For 5 minutes, the paddles may be operated at high speed. The solution would sit unanimated for 15 minutes followed by a 5-minute high-speed paddle step. The solution would be ported off (and could be sampled for residual calcium). This step could be repeated as necessary.

Since demineralization products are usually freeze-dried, the tissue would be removed from the bag system for freeze-drying process or processes. The freeze-drying process is not a part of the bag system/blender system technology.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A system for cleaning and disinfecting allograft material, the system comprising:
   a sterile bag having an outer wall configured to withstand compressive forces, a pair of paddle contact sections, and an allograft retaining section separate from the paddle contact sections;
   a motorized paddle blender having at least two paddles, each having a compressive surface configured to apply compressive forces onto the sterile bag at the pair of paddle contact sections, a motorized portion to actuate the at least two paddles, and a door component configured to hold the sterile bag adjacent the at least two paddles, wherein the at least two paddles and the allograft retaining section are configured to prevent the at least two paddles from compressing the allograft material when the compressive forces are applied onto the sterile bag at the pair of paddle contact sections; and
   a hollowed port system within each of the at least two paddles, the hollowed port system comprising inflow and outflow ports in fluid communication with a hollow interior of each of the at least two paddles, wherein throughout an actuation cycle of the at least two paddles, temperature-controlled solution constantly flows into each of the inflow ports, across the compressive surfaces of each of the at least two paddles, and out each of the outflow ports, providing a constant flow of the temperature-controlled solution across the compressive surfaces of each of the at least two paddles such that the compressive surfaces resist frictional heating and maintain a constant temperature throughout the actuation cycle; and
   further comprising an internal screen defining the allograft retaining section at a central location between the pair of paddle contact sections, the central location defined by the internal screen configured to retain the allograft tissue between the pair of paddle contact sections to prevent tissue pummeling and to allow turbulent fluid flow therethrough, wherein the door component, the at least two paddles, the pair of paddle contact sections, and the central location of the allograft retaining section are configured with respect to one another to locate the compressive forces onto the sterile bag on the pair of paddle contact sections at positions away from the central location of the allograft retaining section so as to in turn provide a non-contact area at the central location to prevent application of the compression forces to the allograft material.

2. A system in accordance with claim 1, wherein the sterile bag is a paddle blender bag having modifications to provide the allograft retaining section separate from the pair of paddle contact sections.

3. A system in accordance with claim 1, wherein the at least two paddles are separated by a given distance to apply the compressive forces on the sterile bag at the pair of paddle contact sections, and wherein the allograft retaining section has a width less than the given distance separating the at least two paddles so as to allow the allograft retaining section to retain the allograft material between the pair of paddle contact sections corresponding to the at least two paddles.

4. A system for cleaning and disinfecting allograft material, the system comprising:
   an ultrasonic water bath containing an amount of agitated fluid to receive and submerge a sterile bag mounted within a motorized paddle blender, wherein:
   the sterile bag has an outer wall configured to withstand blending forces, at least one paddle contact section, and an allograft retaining section separate from the at least one paddle contact section; and
   the motorized paddle blender has at least one paddle configured to apply blending forces onto the sterile bag at the at least one paddle contact section, a motorized portion to actuate the at least one paddle, a door component configured to hold the sterile bag adjacent the at least one paddle, and an exterior inlet port and an exterior outlet port fluidly coupled with an exterior of the motorized paddle blender and located such that the agitated fluid flows through the exterior inlet port from the ultrasonic water bath into the motorized paddle blender, across the outer wall of the sterile bag, and through the exterior outlet port back into the ultrasonic water bath, wherein the at least one paddle and the allograft retaining section are configured to prevent the paddle from contacting the allograft material when the blending forces are applied onto the sterile bag at the at least one paddle contact section.

5. A system in accordance with claim 4, wherein the ultrasonic water bath is configured to control temperature of the allograft material.

6. A system in accordance with claim 5, wherein the ultrasonic water bath is configured to transmit ultrasonic vibrations through the outer wall of the sterile bag to supplement mechanical washing of the allograft material with forces of fluid created by the at least one paddle.

7. A system in accordance with claim 4, further comprising an internal screen defining the allograft retaining section at a location adjacent to the at least one paddle contact section, the location defined by the internal screen configured to retain the allograft tissue adjacent to the paddle contact section to prevent tissue pummeling and to allow turbulent fluid flow therethrough, wherein the door component, the at least one paddle, the paddle contact section, and the location of the allograft retaining section are configured with respect to one another to locate the blending forces onto the sterile bag on the paddle contact section at a position away from the allograft retaining section so as to in turn provide a non-contact area at the allograft retaining section to prevent application of the blending forces to the allograft material.

\* \* \* \* \*